United States Patent [19]

Valentini et al.

[11] Patent Number: 5,939,323
[45] Date of Patent: Aug. 17, 1999

[54] HYALURONAN BASED BIODEGRADABLE SCAFFOLDS FOR TISSUE REPAIR

[75] Inventors: Robert F. Valentini, Cranston; Hyun D. Kim, Providence, both of R.I.

[73] Assignee: Brown University, Providence, R.I.

[21] Appl. No.: 08/864,709

[22] Filed: May 28, 1997

Related U.S. Application Data

[60] Provisional application No. 60/018,492, May 28, 1996.

[51] Int. Cl.⁶ .............................. C12N 5/00; A61F 2/00; A61F 2/28
[52] U.S. Cl. ............................ 435/395; 424/426; 623/16
[58] Field of Search ............................. 435/395; 623/16, 623/18, 66, 11, 22; 433/173, 201.1; 536/55.1; 424/426, 443, 489, 490, 901

[56] References Cited

U.S. PATENT DOCUMENTS

| | | | |
|---|---|---|---|
| 5,336,767 | 8/1994 | Della Valle et al. | 536/55.1 |
| 5,366,508 | 11/1994 | Brekke | 623/16 |
| 5,556,429 | 9/1996 | Felt | 623/16 |
| 5,616,568 | 4/1997 | Pouyani et al. | 514/54 |
| 5,759,205 | 6/1998 | Valentini | 623/16 |

FOREIGN PATENT DOCUMENTS

| | | |
|---|---|---|
| 0 216 453 | 4/1987 | European Pat. Off. . |
| 462426 | 5/1991 | European Pat. Off. . |
| WO93/11803 | 6/1993 | WIPO . |
| WO94/17840 | 8/1994 | WIPO . |
| 9505083 | 2/1995 | WIPO . |
| WO95/19796 | 7/1995 | WIPO . |
| 0784985A1 | 4/1996 | WIPO . |
| WO96/10426 | 4/1996 | WIPO . |

OTHER PUBLICATIONS

"Perry'Chemical Engineers' Handbook", Green, Ed. 6th edition, (1984) (McGraw–Hill: NY), pp. 6–32 and 6–35.

Patterson, R., et al., "Effects of Radiofrequency Glow Discharge . . . to Polyurethane", *ASAIO J*, (Jul. –Sep. 1995), 41:3:625–9.

Walsh, W., et al., "Controlled release of platelet–derived growth factor using ethylene vinyl . . . stainless–steel wires" *Biomaterials*, (1995), 16:1319–1325.

Walsh, W., et al., "Human Osteoblast Response to PTFE Surfaces", *Clinical Materials*, (1994), 16:201–210.

Valentini, R., et al., "Patterned neuronal attachment and outgrowth on surface modified . . . fluoropolymer substrates", *J. Biomaterial Science Polymer Edn.*, (1993), 5:1/2 pp. 13–36.

Benedetti, L., et al., "Dosage Forms From Polymeric Prodrugs: Hydrocortisone Esters of Hyaluronic Acid", *New Polymeric Mater.*, (1991), 3:1:41–48.

Mikos, A., et al., "Laminated Three–Dimensional Biodegradable Foams for Use in Tissue Engineering", *Biomaterials*, (1993), 14:5:323–330.

Freed, L., et al., "Neocartilage Formation in Vitro and in Vivo Using Cells Cultured on Synthetic Biodegradable Polymers", *J. Biomedical Mat. Res.*, (1993), 27:11–23.

Mikos, A., et al., "Wetting of Poly(L–Lactic Acid) and Poly(DL–Lactic–co–Glycolic Acid) Foams for Tissue Culture", *Biomaterials*, (1994), 15:1:55–58.

Kim, W., et al., "Bone Defect Repair with Tissue–Engineered Cartilage", *Bone Defect Repair*, (1993), 94:5:580–584.

Benedetti, L., "Biocompatibility and Biodegradation of Different Hyaluronan Derivatives (Hyaff) Implanted in Rats", *Biomaterials*, (1994), 14:1154–1160.

Freed, L., et al., "Joint Resurfacing using Allograft Chondrocytes and Synthetic Biodegradable Polymer Scaffolds", *J. Biomedical Mat. Res.*, (1994), 28:891–899.

Robinson, B., et al., "Calvarial Bone Repair with Porous D, L–Polylactide", *Otolaryngol Head Neck Surg*, (1995), 112:707–713.

Chu, C., et al., "In Situ Assessment of Cell Viability within Biodegradable Polylactic Acid Polymer Matrices" *Biomaterials*, (1995), 16:18:1381–1384.

Mooney, D., et al., "Biodegadable Sponges for Hepatocyte Transplantation", *J. Biomedical Mat. Res.*, (1995), 29:959–965.

Chu, C., et al., "Articular Cartilage Repair using Allogeneic Perichondrocyte–Seeded Biodegradable Porous Polylactic Acid (PLA): A Tissue–Engineering Study", *J. Biomedical Mat. Res.*, (1995), 29:1147–1154.

Attawia, M., et al., "Immunofluorescence and Confocal Laser Scanning Microscopy Studies of Osteoblast Growth and Phenotypic Expression in Three–Dimensional Degradable Synthetic Matrices", *J. Biomedical Mat. Res.*, (1995), 29:843–848.

Nicoll, S., et al., "In Vitro Characterization of Transforming Growth Factor –β1–Loaded Composites of Biodegradable Polymer and Mesenchymal Cells", *Cells and Materials*, (1995), 5:3:231–244.

Hollinger,. J., et al., "Poly(α–Hydroxy Acids): Carriers for Bone Morphogenetic Proteins" *Biomaterials*, (1996), 17:187–194.

Pineda, L., "Bone Regeneration with Resorbable Polymeric Membranes" *J. Biomedical Mat. Res.*, (1996),31:385–394.

Kim, H., et al., "Hyaluronan–Based Biodegradable Scaffolds for Skeletal Tissue Reconstruction", *Fifth World Biomaterials Congress*, (1996), p. 236. Toronto Canada.

Lo, H., et al., "Poly(L–Lactic Acid) Foams with Cell Seeding and Controlled–Release Capacity", *J. Biomedical Mat. Res.*, (1996), 30:475–484.

Schugens, C., et al., "Polyactide Macroporous Biodegradable Implants for Cell Transplantation . . . " *J. Biomedical Mat. Res.*, (1996), 30:449–461.

*Primary Examiner*—Jean C. Witz
*Assistant Examiner*—Susan Hanley
*Attorney, Agent, or Firm*—Wolf, Greenfield & Sacks, P.C.

[57] ABSTRACT

A hyaluronic acid derivitized scaffold and method of forming are disclosed. The scaffolds are useful for various medical purposes such as tissue repair, tissue reconstruction and wound healing. In order to enhance these processes the scaffolds may be engineered to incorporate biologically active molecules such as BMP.

8 Claims, 1 Drawing Sheet

HYALURONAN BASED BIODEGRADABLE SCAFFOLDS FOR TISSUE REPAIR

RELATED APPLICATIONS

This application claims priority under 35 USC § 119(e) from U.S. provisional patent application Ser. No. 60/018,492 filed on May 28, 1996, entitled Hyaluronan Based Biodegradable Scaffolds for Tissue Repair. The contents of the provisional application are hereby expressly incorporated by reference.

BACKGROUND OF THE INVENTION

Hyaluronic acid is a naturally occurring mucopolysaccharide consisting of alternating D-glucuronic acid and N-acetyl D-glucosamine monomers. It is present in connective tissues and plays a vital role in many biological processes such as tissue hydration, proteoglycan organization in the extracellular matrix, and cell differentiation. Because of its important biological roles, hyaluronic acid has been widely exploited in medical practice for use in treating many different conditions. Several hyaluronic acid containing products are currently marketed for pharmaceutical or veterinary use, including a product for intra-ocular injection during eye surgery, synovitis agents for veterinary use, and coated gauzes for wound dressings.

Through the esterification of carboxyl groups of hyaluronic acid with various therapeutically inactive and active alcohols, it has been possible to synthesize biopolymers with medically desirable properties that are significantly different from those of hyaluronic acid itself. The biocompatibility of these altered molecules appears to be quite good. For example, a chemically modified form of hyaluronic acid "HYAFF-11" prevents fast enzymatic degradation in vivo and degrades slowly in concert with new tissue formation. The HYAFF-11 material is commercially available as skin repair products for wound and burn patients.

The following depicts the structure of hyaluronic acid.

scaffolds are biocompatible and have degradation products that are substantially non-toxic. These products are an improvement over prior art materials such as polylactide, polyglycolide, their copolymers, and the like which, although biocompatible, render acidic degradation products that are not necessarily optimal for tissue repair.

The porous scaffolds of the invention can be fabricated to any size or shape and can be produced to virtually any desired predetermined pore size, depending upon the application. The scaffolds of the invention can be adapted to promote host cells of different varieties to migrate, adhere, proliferate, differentiate, and synthesize new tissue inside the pores. The invention can accelerate the infiltration and integration of host tissue, while degrading slowly in concert with new tissue formation. In addition, the porous scaffold can be used as a substrate for covalent or non-covalent attachment of bioactive molecules such as cytokines, peptides, proteins, etc. that have specific effects on ingrowing cells or surrounding tissue. Depending upon the bioactive molecules selected, these effects on ingrowing cells can be directed to enhancing cell migration, adhesion, commitment, proliferation and/or differentiation.

According to one aspect of the invention, a method for forming a substrate for cell growth is provided. A water-insoluble hyaluronic acid derivative is dissolved in a first solvent. A mixture of the first solvent, the water-insoluble hyaluronic acid derivative and a pore forming agent is formed, wherein the pore forming agent is insoluble in the first solvent. The mixture then is contacted with a second solvent, wherein the water-insoluble hyaluronic acid derivative is insoluble in the second solvent, but the pore forming agent is soluble in the second solvent, whereby the first solvent and the pore forming agent are extracted from the mixture to produce a porous scaffold of the water-insoluble hyaluronic acid derivative.

The pore forming agent preferably is sized so as to leave pores sufficient to permit cell ingrowth into the scaffold when the pore forming agent is extracted from the mixture.

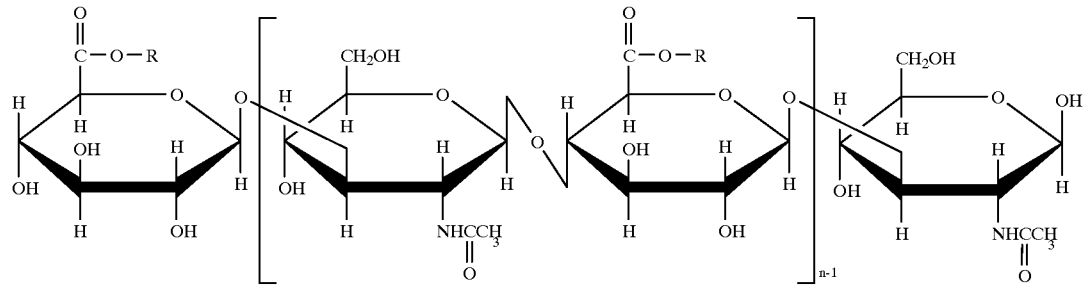

The carboxyl group of hyaluronic acid can be replaced with various moieties, including molecules such as ethyl, propyl, pentyl, benzyl or larger molecules such as hydrocortisone or methyl prednisolone. Reaction conditions can be controlled so as to influence the degree of substitution on the hyaluronic acid molecule, thereby further influencing the properties of the final product.

SUMMARY OF THE INVENTION

The invention utilizes derivatives of hyaluronic acid as raw material to fabricate porous, degradable scaffolds for a variety of medical purposes, including, but not limited to, tissue repair and reconstruction and wound healing. These The resulting scaffold is a three-dimensional structure of interconnected pores which permit cell ingrowth and, eventually, tissue replacement of the scaffold. In one particularly preferred embodiment, the pore forming agent is particles having a diameter between 10–1000 micrometers with optimal tissue ingrowth at 106 and 600 micrometers.

It further is preferred to vacuum dry the scaffold from a wet state at a temperature of between 4° C. and 30° C., most preferably at ambient or room temperature. This results in a scaffold that is non-brittle, handleable, and capable of being autoclaved with steam or gas without undesirably affecting the pore interconnectivity of the scaffold. Most preferably the water-insoluble hyaluronic acid derivative is hyaluronic acid esterified with a benzyl moiety.

In further embodiments, the method involves agents which are attached to the scaffold. The attachment may be covalent or non-covalent attachment. The attachment may be directly to the hyaluronic acid derivative in advance of the scaffold formation, or may be applied covalently or non-covalently after the formation of the scaffold, such as by a coating. The agent also may be blended with the dissolved hyaluronic acid derivative in the first solvent, to cause the agent to be intermixed with and part of the formed scaffold structure. The kinds of agents contemplated for attachment to the scaffold include drug agents for being released to surrounding tissues, antipathogens for inhibiting pathogenic invasion of the scaffold, cell stimulating agents for causing, for example, cell migration, adhesion, commitment, proliferation and/or differentiation in, on or within the scaffold, and bioerodable coatings or blending agents for influencing the bioerodability of the scaffold and/or for containing any of the foregoing agents such as antipathogen agents, drug agents or cell stimulating agents.

According to another aspect of the invention, a substrate for cell growth is provided. The substrate is a scaffold of water-insoluble derivatized hyaluronic acid defining interconnected pores of sufficient size to permit mammalian cell ingrowth into the pores, wherein the derivatized hyaluronic acid is a covalent conjugate of hyaluronic acid and a water-insoluble moiety that renders the conjugate insoluble in water. The preferred features of the scaffold are as described above in connection with the methods. All the various products resulting from the foregoing methods are intended to be embraced by this aspect of the invention. For example, scaffolds coated non-covalently or covalently with bioactive agents are contemplated by the invention. Likewise, scaffolds coated with or blended with bioerodable polymers are contemplated by the invention. The preferred covalent conjugate of hyaluronic acid is esterified with benzyl moieties, most preferably wherein 100% of the carboxyl moieties of the hyaluronic acid are esterified with benzyl moieties. Scaffolds composed of hyaluronic acid esterified with other moieties (e.g. drugs, peptides) may also be employed.

According to another aspect of the invention, a two-phase scaffold is provided. The two-phase scaffold is prepared by adding a hydrogel, a biodegradable polymer such as polylactic acid (PLA) or polyglycolic acid (PGA), or a ceramic such as hydroxyapatite or tricalcium phosphate to a hyaluronic acid solution. Preferably the hyaluronic acid solution is HYAFF and the two-phase scaffold is prepared with a hydrogel. The pores of the two-phase scaffold are filled with the hydrogel. The two-phase scaffold has all of the preferred features as described above in connection with the single-phase scaffold of the invention.

According to another aspect of the invention, methods for growing cells are provided. These cells are contacted with the scaffold of the invention as outlined above, and permitted to grow upon and/or into the pores of the scaffold.

According to another aspect of the invention, methods of stimulating cell differentiation are provided by contacting cells with the scaffold of the invention.

According to another aspect of the invention, methods for tissue culture are provided by contacting cells with the scaffold of the invention.

According to still other aspects of the invention, methods for treating a variety of conditions are provided, including methods for reconstituting or repairing bone, methods for accelerating wound healing, methods for repairing cartilage as well as methods for reconstituting tissues in the ectodermal, mesodermal and endodermal layers that require replacement or regeneration.

Scaffolds with cells seeded upon the scaffolds also represent an aspect of the invention. One particularly important aspect of the invention is the stimulation of bone cells such as osteoblasts and pre-osteoblasts, and precursors thereof, to grow within a scaffold which can be precoated, dipped or filled with bone morphogenetic proteins in order to induce bone growth and differentiation from bone precursor cells.

These and other aspects of the invention will be described in greater detail below.

DETAILED DESCRIPTION OF THE INVENTION

Figure 1:
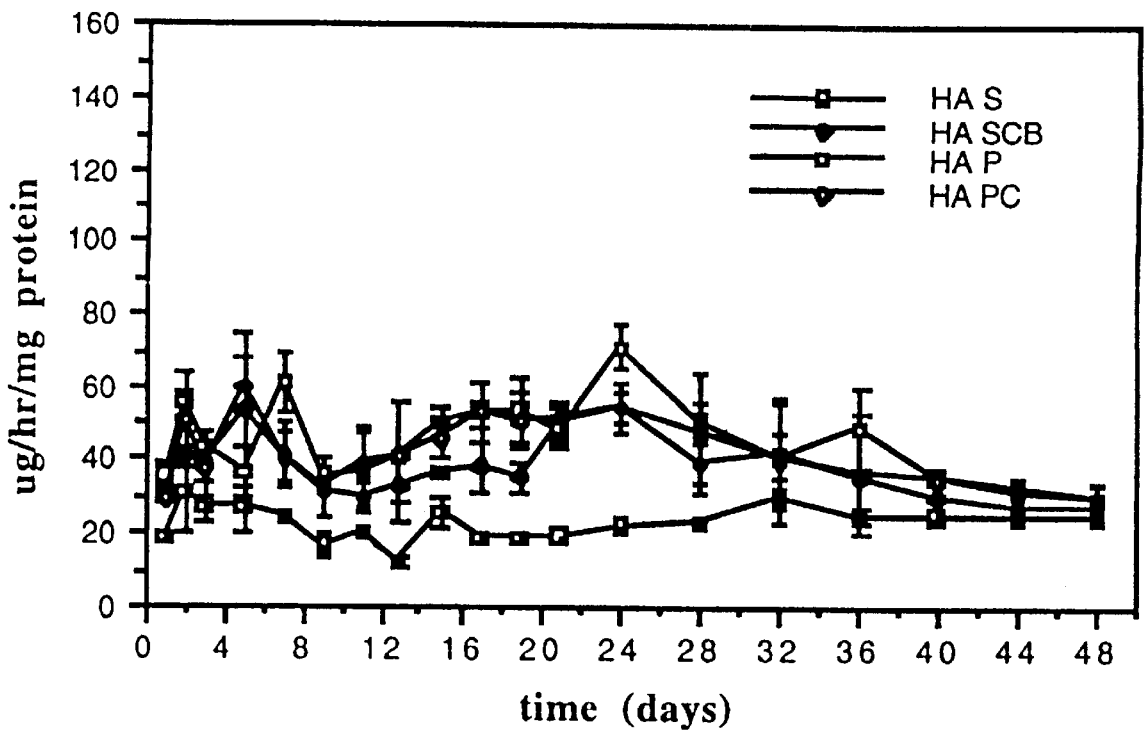
FIG. 1 is a graph depicting the release of BMP from Hyaluronic Acid scaffolds, prepared as a scaffold alone (HA S), as a scaffold precoated with BMP and dried (HA P), as a scaffold in which BMP and collagen are gelled together (HA SCB), and a scaffold in which the scaffold is precoated with BMP and then collagen (HA PC)

The invention involves three-dimensional biodegradable scaffolds of hyaluronic acid derivatives for tissue reconstruction and repair. The porous scaffold has interconnected pores that permit cells to grow into the scaffold, preferably completely penetrating the scaffold with cells, and thereby, eventually replacing the scaffold with tissue. The scaffold can be fabricated to be virtually any shape, size or thickness, and can be produced to various porosities and pore sizes, depending upon the application. The scaffold is degradable, so that eventually it can be completely replaced by tissue. The scaffold degrades slowly in concert with new tissue formation. Such a scaffold offers the advantage of promoting host cells to migrate, adhere, proliferate and synthesize new tissue inside the pores, accelerating, for example, wound healing.

Void volumes for the scaffold according to the invention can range from 40–90%. Pore sizes for the scaffold of the invention can range from 10–1000 micrometers.

The invention requires the use of hyaluronic acid derivatives that are water-insoluble, but are soluble in a first solvent. The water-insoluble hyaluronic acid is dissolved in that first solvent, together with a pore forming agent that is insoluble in the first solvent. That mixture then is contacted with a second solvent in which the hyaluronic acid derivative is insoluble but in which the pore forming agent is soluble. In this manner, the first solvent is replaced/extracted by the second solvent in which the hyaluronic acid is insoluble, bringing the hyaluronic acid derivative out of solution and forming a scaffold. Likewise, the pore forming agent is soluble in the second solvent and is extracted/dissolved, thereby leaving a porous scaffold of the water-insoluble hyaluronic acid derivative.

The water-insoluble hyaluronic acid derivatives are known to those skilled in the art and described in numerous publications. For example, because hyaluronic acid is a polycarboxylic acid, its water-insoluble esters may be prepared using standard methods for the esterification of carboxylic acids, such as the treatment of free hyaluronic acid with the desired water-insoluble moieties in the presence of appropriate catalysts. Alternatively, the esters may be prepared by treating a quaternary ammonium salt of hyaluronic acid with an esterifying agent in a suitable aprotic solvent. Details of this latter method have been described in European Patent Application No. EP216453, Apr. 1, 1987, the disclosure of which is incorporated herein by reference. Esterification of hyaluronic acid with suitable water-insoluble moieties may be achieved also by the use of linking groups interposed between the hyaluronic acid and the water-insoluble moiety.

Likewise, hyaluronic acid may be derivatized via amide bonds, as will be clear to those skilled in the art. Such hyaluronic acid derivatives are described in the following PCT publications, the disclosure of which is incorporated herein by reference. WO95/24429 discloses highly reactive esters of carboxy polysaccharides, including hyaluronic acid. PCT Patent applications WO95/24497 and WO95/04132 disclose methods for preparing high molecular weight hyaluronic acid derivatives.

Hyaluronic acid is a linear polysaccharide. Many of its biological effects are a consequence of its ability to bind water, in that up to 500 ml of water may associate with 1 gram of hyaluronic acid. Esterification of hyaluronic acid with uncharged organic moieties reduces the aqueous solubility. Complete esterification with organic alcohols such as benzyl renders the hyaluronic acid derivatives virtually insoluble in water, these compounds then being soluble only in certain aprotic solvents.

When films of hyaluronic acid are made, the films essentially are gels which hydrate and expand in the presence of water (hydrogels). By esterifying the hyaluronic acid and making it insoluble in water, the scaffolds of the present invention then are possible. The scaffolds are not hydrated in the presence of water and maintain their overall structure, permitting cell ingrowth. Thus, the hyaluronic acid derivatives useful according to the invention are those sufficiently derivatized such that the hyaluronic acid derivative will not form a hydrogel. Those of ordinary skill in the art can easily test whether sufficient derivitization with an uncharged moiety has occurred so as prevent the formation of a hydrogel. The preferred hyaluronic derivative is 100% esterified hyaluronic acid-benzyl covalent conjugates, sold under the trade name HYAFF by Fidia Advanced Biopolymers, Abano Terme, Italy.

Solvents for the water-insoluble derivatized hyaluronic acid molecules include dimethylsulfoxide (DMSO), N-methyl-pyrrolidone (NMP), 1, 1, 1, 3, 3, 3-hexafluoro-2-propanol (HFIP) and dimethylacetamide (DMAC). Other appropriate solvents will be known to those of ordinary skill in the art. NMP is the preferred solvent.

Non-solvents for the derivatized hyaluronic acid useful in the invention include water, ethanol, isopropanol, glycerol, ethyl acetate, tetrahydrofuran, and acetone. Other non-solvents will readily be known to those of ordinary skill in the art. To be clear, the non-solvent ("second solvent") is used to replace the solvent and cause the extraction of the first solvent such as NMP or DMSO, thereby causing the formation of the scaffold and to dissolve the pore forming agent, thereby producing pores in the scaffold.

The pore forming agents useful in the invention are particles of a desired size that are insoluble in the first solvent but that are soluble in the second solvent The particles preferably are sized and are present in sufficient concentration so as to create pores of a sufficient size to permit a plurality of mammalian cells to grow into and throughout the interconnected pores. In one particularly preferred embodiment involving bone growth, the particles are between 100 and 600 micrometers in diameter. The pore forming agents may be any of a variety of materials, depending on the particular selection of the solvent and non-solvent. Examples include: salt crystals such as NaCl, KCL, $MgCl_2$, $CaCl_2$ and $BaSO_4$; soluble proteins such as albumin, globulins, and the like; soluble dextrans such as dextran and dextransulfates, and the like; soluble hydrogels such as agarose, alginate, chitosan, cellulose, carboxymethylcellulose, and the like; and microspheres of polylactic acid, polyglycolic acid, and the like. Those of ordinary skill in the art will readily be able to select useful pore forming agents. Tables 1, 2, and 3 in the Examples provide examples of the use of different sizes and concentrations of NaCl as well as various lyophilization techniques to produce a variety of pore sizes and shapes.

As mentioned above, the scaffolds may be coated with a variety of materials, including bioactive agents, and bioerodable agents. Bioactive agents include antipathogenic agents such as antibiotics, antivirals, and antifungals, anti-inflammatory agents, immunomodulators, cytokines, etc. Virtually any bioactive compound useful in the scaffold or in the environment of the scaffold may be coated onto the scaffold. In one particularly important embodiment, bioactive molecules that have specific effects on ingrowing cells are coated onto the scaffold. Such molecules can be those that effect cell migration, cell adhesion, cell commitment, cell proliferation, cell differentiation, etc. Such molecules include interlukins, interferons, bone morphogenetic factors, growth factors including platelet-derived growth factor, epidermal growth factor, transforming growth factor and fibroblast growth factor and colony stimulating factors. In one important aspect of the invention, the scaffold is coated with bone morphogenetic proteins (BMPs) or growth and differentiation factors (GDFs) in order to induce the formation of differentiated bone cells from bone precursor cells.

The coating also can be a biodegradable polymer which is added to influence the degradation rate of the scaffold. Biodegradable polymers useful according to the invention include polylactic acid, polyglycolic acid, polylactic-polyglycolic copolymers, polycaprolactone, polyphosphazenes and polyorthesters. Other biodegradable polymers are well known to those of ordinary skill in the art and are described in great detail in the art relating to tissue implants and sustained release polymeric devices.

Instead of coating the scaffold with the foregoing polymer materials a two-phase scaffold may be prepared, in which the scaffold pores may be filled with the foregoing materials or a hydrogel or ceramic. The two-phase scaffold may be prepared as described below in Example 5. The two-phase scaffold has all of the preferred features as described above in connection with the single-phase scaffold of the invention.

As mentioned above, the materials may be non-covalently coated on the scaffolds or covalently attached to the scaffolds. If covalently attached to the scaffolds, such covalent attachment may be carried out prior to the formation of the scaffold or may be carried out after formation of the scaffold. Drugs may be incorporated in a gel which solidifies within the scaffold (e.g. collagen type I).

Many of the objects and advantages described above in connection with coatings may be achieved by blending such materials in solution with the water-insoluble hyaluronic acid derivative prior to formation of the scaffold. For example, biodegradable polymers may be included in such solutions, with the resulting scaffold being a blend of the derivatized hyaluronic acid and the biodegradable polymer. Likewise, bioactive molecules may be blended with the water-insoluble hyaluronic acid derivative prior to formation of the scaffolding. When a biodegradable polymer is blended with the hyaluronic acid derivatives of the invention, then it is preferred that the biodegradable polymer comprise less than 50% of the total material of the scaffold, and more preferably 10% or less of the total material of the scaffold. In any event, the nature of the biodegradable polymer and amount must be adjusted, depending upon the hyaluronic acid derivative selected and the desired characteristics of the end product so that the final scaffold has the characteristics desired for the particular application. The biodegradable polymer of this embodiment, however, should be chosen so that it is not dissolved by the water or other non-solvent. If the biodegradeable polymer is soluble, it may be chemically modified to make it insoluble. Techniques for chemical modification are well known to those of skill in the art.

It is preferred that the scaffold be dried from the wet state by lyophilization without freezing. In other words, a vacuum pressure is applied to dry the scaffold. It is preferred that the vacuum pressure be applied at about ambient or room temperature, because doing so at either an elevated temperature or by freeze-drying adversely affects the interconnectivity of the pores and the overall structure of the scaffold. According to the methods of the invention, scaffolds are produced with not only desirable porosity for cell ingrowth, but also with a structural integrity so that they may be sterilized using steam or gas sterilization without adversely affecting the scaffold structure and characteristics.

The scaffolds of the invention have a variety of clinical uses. One important example is in the repair of bone defects caused by trauma, bone tumor resection, in the case of joint fusion and spinal fusion for non-healing fractures and osteoporotic lesions. It is noted that the scaffold may be seeded with bone cells (osteoblasts and osteocytes) and bone cell precursors (mesenchymal stem cells from bone marrow, periosteum, endosteum, etc.) before implantation. The scaffolds also may be used in treating tooth and jaw defects in cases of trauma, bone loss, tooth loss, gum disease and the like. The scaffold again can be seeded with cells of the foregoing type for such purposes. The scaffolds also are useful in treating cartilage defects such as those which result from rheumatoid arthritis, osteoarthritis and trauma. Cells useful for seeding in such circumstances are chondroblasts and chondrocytes and cartilage cell precursors such as the cell precursors described above in connection with bone. The scaffolds also may be used to repair defects and damage in skin, muscle and other soft tissues such as results from trauma, burns, ulcers (diabetic ulcers, pressure sores, venus, stasis ulcers, etc.). In this case, scaffolds can be seeded with, for example, dermal fibroblasts, keratinocytes, and skeletal muscle cells. Likewise, damage to visceral organs including liver damage, heart attack damage, and damage resulting from intestinal cancer or intestinal ulcer may be treated with the scaffolds of the invention. In these instances, the scaffolds can be seeded with cells such as hepatocytes, cardiac muscle cells, intestinal cells, etc.

The invention also pertains to in vitro culture of cells with the purpose of creating tissue constructs for repairing tissues and organs in vivo. The scaffolds may be used to promote tissue culture of committed cells and/or differentiation of precursor cells. Thus, the scaffolds of the invention can be used in virtually all instances when it is desirable to provide a substrate for the growth of cells onto or into a tissue replaceable matrix. Scaffolds can also be used with autografts, allografts, and xenografts associated with bone grafts, cartilage grafts, and joint resurfacing implants and are particularly important applications of the present invention.

EXAMPLES

Example 1

Preparation of Polymer Scaffolds.

1. Scaffold preparation:

a) HYAFF-11 Scaffold Fabrication Technique:

HYAFF-11, a 100% esterified derivative of hyaluronic acid (commercially available from Fidia Advanced Biopolymers, Abano Terme, Italy) was dissolved in N-methyl pyrrolidone for 12 hours at room temperature to make a 10% (w/v) solution. Presieved NaCl crystals (Fisher Scientific, or Sigma) were mixed for 10 minutes at 20° C. with the polymer solution at salt to polymer dry weight ratio of 9:1 or 15:1 (w/w) to create a slurry or a paste-like mixture. The size and quantity of NaCl used determines the porosity, pore distribution, and interconnectivity of the final scaffold product. The quantity used in each experiment, therefore, was adjusted in order to produce a scaffold having the desired porosity, pore distribution, and interconnectivity. The average porosity, pore distribution, and interconnectivity produced at particular concentrations of NaCl is depicted in Table 1. The final scaffold pore size is dependent on the size of the NaCl crystals used and, therefore, the size of the NaCl crystals to be used was determined based on the desired pore size. The desired size of NaCl used ranged anywhere between 106 and 600 um. The effect of different lyophilization techniques on pore formation is presented in Table 2. Average pore size produced at particular concentrations of NaCl is depicted in Table 3.

TABLE 1

| Salt content (salt-polymer ratio) | None | 2:1 | 9:1 | 15:1 | 25:1 |
|---|---|---|---|---|---|
| Interconnecting Pores | No | No | Yes | Yes | Yes |
| Septum Thickness | None | None | Thick | Thin | Very Thin |
| Void Volume | None | <5% | 60–75% | 65–85% | 75–90% |

TABLE 2

| Lyophilization Technique | No lyoph. | Freeze/lyoph. | Air Dry | Lyophilize wet |
|---|---|---|---|---|
| Status of Pores | No interconnecting pores | No interconnecting pores | No interconnecting pores | Interconnecting pores |

TABLE 3

| Salt size (μm) | None | 100–600 | 200–400 | 400–600 |
|---|---|---|---|---|
| Pore size (μm) | <20 | 50–750 | 150–500 | 350–700 |

The paste was then formulated into scaffolds utilizing either of the two following techniques.

(1). The paste was packed into rubber molds which were submerged in a 1 liter bath of distilled water for 48 hours at 20° C. and stirred gently. The water was changed frequently (preferably every 8 hours). The water serves both as a nonsolvent which is capable of absorbing organic solvent and as a pore former which dissolves the NaCl, leaving pores in the scaffold. The resulting wet scaffold was lyophilized at room temperature for 24 hours, without drying, in order to obtain maximum pore interconnectivity with characteristic ultrathin septa between pores. It was observed that freezing or air drying greatly diminishes the ability of the scaffold to exhibit optimal pore characteristics. The dry scaffolds were then trimmed and cut to desired shape and size.

(2). The paste was packed into rubber molds which were submerged in 1 liter of 100% ethanol at 20° C., a nonsolvent, for 24 hours with frequent change of ethanol. Ethanol only absorbs the organic solvent while leaving the salt crystals intact. The scaffold was then cut or pressed into the desired shape or size (alternatively the scaffold was cut and shaped after the incubation with water). Pore formation was achieved next by submerging the scaffold in 1 liter distilled water for 24 hours. The water was changed every 8 hours. It was observed that the scaffold begins to float during the final stages of salt leaching. The resulting wet scaffold was lyophilized to dryness.

The final scaffold was then sterilized either by standard ethylene oxide gas sterilization or steam autoclave at 250° F. for 30 minutes with a 15 minute dry cycle, after which it was used for in vitro cell seeding or in vivo implantation.

b) HYAFF-11p75 Scaffold Fabrication Technique:

Polymer scaffolds are prepared from HYAFF-11p75, a 75% esterified form of hyaluronic acid using the following technique.

A known amount of HYAFF-11p75 is dissolved (12 hours, room temp.) in an organic solvent (preferably dimethyl sulfoxide, DMSO) to make a 10% (w/v) solution. Presieved NaCl crystals of desired size or size ranges (narrow or wide ranges, anywhere between 106–600 um) are mixed (5 min., room temp.) With the polymer solution at salt to polymer dry weight ratio of 9:1 or 15:1 (w/w) to create a slurry or a paste-like mixture. The paste is packed into rubber molds and submerged in 100% ethanol for 48 hours with frequent change of EtOH. Pore formation is achieved next by submerging the scaffolds in distilled water (1 L) with stirring for 30 minutes with frequent change of water. Water treatment is stopped when the foams have floated and expanded slightly. HYAFF-11p75 loses integrity and structure if left in water for extended periods of time, but 30 minutes has been found to be enough time for complete salt leaching while maintaining scaffold structure and integrity. The slight expansion causes NaCl to be leached out much faster than HYAFF-11 scaffolds. The resulting wet scaffold is lyophilized and trimmed.

2. Treated Scaffold preparation:

In some experiments, the scaffold was dipped, injected, chemically immobilized, or sprayed with drugs, peptides, proteins, cytokines, growth factors, oligonucleotides, antisense oligonucleotides, DNA, or polymers prior to in vitro or in vivo application. This process formulated a hybrid structure that, depending on the molecule or polymer used, targeted cell migration, adhesion, commitment, proliferation, or differentiation. The following non-limiting examples of treated scaffolds were prepared.

a) Bone morphogenic protein scaffolds: Scaffolds were produced as described above except that 10 μg of recombinant human bone morphogenic protein (rhBMP) was adsorbed on to the scaffold by dip coating the scaffold with a 0.1–1000 μg/ml BMP solution and air drying for 30 minutes in a laminar flow hood. Alternatively, 0.1–1000 μg/ml BMP in collagen type I suspension at 4° C. was added to the scaffold and then gelled at 37° C. for 1 hour.

b) Dipped protein scaffolds: The preformed scaffold was dipped in a solution containing a drug. A small volume of fluid (e.g. solvent, such as water, DMSO, etc.) containing a known amount of drug was coated or sprayed onto the scaffold. The solvent was evaporated by airdrying, application of vacuum, lyophilization, etc.

c) Chemical linking of drug to scaffold: A drug was chemically linked to HYAFF scaffold. HYAFF surface is activated with coupling agents which bind to OH, $NH_2$, SH or COOH groups on the HYAFF. The coupling agent which was bifunctional was reacted with OH, $NH_2$, SH or COOH groups on a drug to achieve binding. In one example, CDI (a heterobifunctional coupling agent) in acetone or EDC (a heterobifunctional coupling agent similar to CDI except that it is soluble in water) in water was used to attach to OH groups on the HYAFF. The other end of the EDC or CDI reacted with $NH_2$ or COOH groups on the drug or peptide to achieve covalent linkage.

d) A drug that was soluble in DMSO, NMP, etc. (but insoluble in the non-solvent water, ethanol, etc.) was mixed with the HYAFF/DMSO or NMP, etc. solution so as to achieve incorporation of drug or peptide in the bulk of the HYAFF material. A carrier molecule or excipient (albumin, dextran, carboxymethyl cellulose, etc.) was also incorporated.

e) A drug was added to a preformed HYAFF scaffold by the use of a gel-forming material. For example growth factors, BMPs, etc. were added to liquid collagen gels maintained at 4° C. temperature. The growth factor/liquid gel was coated, dipped or sprayed onto the HYAFF scaffold. The scaffold/gel construct was then warmed to room temp. (20° C.) or higher (body temp. 37° C.) for between 20 minutes and two hours in order to effect gelling and entrapment of the drug or peptide.

f) In some experiments, HYAFF scaffold was also sprayed, dipped or coated with a second polymer including HYAFF, PLLA, PGA, etc., that contained a drug or peptide. This enabled release of the drug and tailoring of scaffold degradation rate.

g) In some experiments, the HYAFF scaffold was also made with degradable microspheres comprised of PLLA, PGA, PLGA, etc., which slowly degraded to form pores. As the pores opened, tissue ingrowth occurred. This approach allowed staged tissue invasion in cases where early ingrowth was to be discouraged (e.g. infection, etc.).

Example 2

In vitro cell growth. proliferation and differentiation on polymer scaffolds.

Polymer scaffolds were fabricated as described in Example 1, using sieved NaCl crystals (212–600 um) and both 9:1 and 15:1 salt to polymer dry weight ratios. The scaffolds were trimmed to produce cylinders having a 5 mm diameter by 3 mm thickness and autoclaved for sterility. The scaffolds were then prewet in 70% ethanol, and rinsed in sterile PBS. Primary rat calvarial osteoblasts isolated from 7 day pups by sequential enzymatic digestion in 1.37 mg/ml/ collagenase/0.25% trypsin were seeded onto scaffolds at a density of 100,000 cells/20 ul media/scaffold. The cells were allowed to penetrate the pores for 30 minutes, prior to the addition of Ham's F12+10% FBS (Gibco or Sigma) alone or supplemented with 50 ug/ml ascorbic acid (Sigma) and 10 mM p-glycerophosphate (Sigma). The cells were maintained in the scaffold apparatus under tissue culture conditions for up to 11 weeks. Cell viability and attachment were assessed by fluorescent microscopy using a Live/Dead Eukolight viability kit (Molecular Probes, Inc., Eugene, Ore.). Under scanning electron microscopy (SEM) and light microscopic evaluation, the polymer scaffolds showed interconnecting pores 200 to 600 microns in diameter. The 15:1 polymer scaffolds showed greater pore interconnectivity and a thinner septum between pores than the 9:1 scaffolds. Pilot studies showed that autoclaving did not alter scaffold geometry or induce degradation. Osteoblasts seeded onto polymer scaffolds remained viable at 1, 6, and 11 weeks as evidenced by greater than 95% fluorescence staining for live versus dead cells. Increased fluorescence intensity at later time points also suggested significant cell proliferation, although this was not quantified. Scaffolds seeded with osteoblasts cultured in ascorbic acid/phosphate supplemented media showed nodules of calcification at 4 weeks and beyond, suggesting that HYAFF scaffolds support differentiation.

Example 3

In vivo cell migration and growth on implanted scaffolds.

In vivo results demonstrated that HYAFF scaffolds can support bone formation. In one study, scaffolds (4 mm diameter, 1 mm thickness) were implanted into 4 mm full thickness rat cranial defects and harvested after 3 weeks. Empty rat cranial defect sites served as negative controls. Upon macroscopic examination after sacrifice, the control empty defect site remained largely devoid of tissue. Histological analysis revealed a thin fibrous connective tissue sheath adjacent to the dural surface and continuous with the original cranial bone. For HYAFF scaffold sites, the implant felt semi-rigid upon examination and was intimately connected with the surrounding cranial bone. Histologically, the entire implant was filled with invading tissue. The polymer scaffold showed minimal signs of degradation. The scaffold pores were completely invaded and contained numerous tightly-packed fibroblastic cells with occasional blood vessels. The newly formed tissue in the pores stained positive for collagen and mineral, as evidenced by fast green and von Kossa staining. In some larger pores islands of bone trabeculae were observed. Trabeculae consisted of a row of osteoblast-like cells over an osteoid seam adjacent to darkly stained mineral matrix. These results provide concrete evidence that HYAFF scaffolds alone are osteoconductive (ability to support bone ingrowth), in bony defects.

Example 4

Peptide treated scaffolds capable of inducing and sustaining cellular differentiation.

Addition of exogenous factors to the scaffold, such as drugs, peptides, or proteins, can additionally enhance target tissue formation, especially for large, non-healing, critical-sized defects. Examples of such drugs, peptides, or proteins are provided in Example 1 above.

Bone morphogenetic proteins (BMPs) are members of the transforming growth factor beta (TGFβ) superfamily proteins involved in the induction of cartilage and bone. These osteogenic and chondrogenic proteins are capable of committing undifferentiated mesenchymal stem cells into bone and cartilage forming cells. Scaffolds adsorbed with 10 ug bone morphogenetic protein (rhBMP-2) were implanted into rat 8 mm diameter critical-sized cranial defects to assess bone formation at a bony site. In addition, similar scaffolds were implanted into subcutaneous tissue to assess ectopic bone formation. After 3 weeks, scaffolds at both sites displayed significant bone formation in pores that were filled with mineralizing tissue, as evidenced histologically with von Kossa staining. BMP-2 scaffolds exhibited more tissue ingrowth and mineralization than untreated scaffolds.

Example 5

Preparation of a two-phase scaffold.

A two-phase scaffold was prepared by adding a hydrogel to the solution instead of adding a soluble crystal, protein, or microsphere to the HYAFF solution. For example, HYAFF was dissolved in DMSO and preformed microspheres were added. Agarose microspheres were formed through a hot-melt techniques and sieved to a size of 100–700 microns. The HYAFF solution and microsphere were mixed and molded into a prescribed shape. The resulting mold was then immersed in a bath of water or ethanol which did not dissolve the microspheres but did extract the solvent. Similarly, the solvent was extracted by drying under ambient conditions, with slightly elevated temperature (<70° C.) and/or with a gentle vacuum. After or during solvent evaporation/air drying the construct was lyophilized to affect full solvent removal and scaffold formation. The resulting scaffold contained entrapped microspheres which constituted 40–90% of the scaffold volume. 70–90% of the void volume contained microspheres with the remainder being empty due to microsphere loss. Following lyophilization, the microspheres were dehydrated and shrank to 5–20% of their original size. The microspheres were rehydrated by immersion in water or placement in tissue. The rehydration resulted in microspheres which were 90–95% of their original starting size (e.g. after initial fabrication). Microspheres were fabricated from a range of hydrogel materials including agarose, alginate, chitosan, collagens type I, IV, etc., Matrigel, laminin, etc. The hydrogel microspheres were also covalently linked with drugs and peptides using the coupling strategy described above. Likewise, drugs or peptides were mixed with the hydrogel during or after microsphere formation. The advantage of a two-phase scaffold is that a range of microspheres containing a range of drugs or peptides (including several different drugs and peptides together) can be incorporated in the scaffold for various purposes (e.g. antibiotics to treat infection, growth factors to stimulate tissue growth, BMPs to stimulate bone or cartilage induction).

Example 6

Comparison of retention of BMP in Hyaluronic acid (HA) versus poly-lactic acid (PLLA) scaffolds.

1. Scaffold Fabrication

Poly-L-lactic acid (PLLA, MW 100 kD; Polysciences, Inc.) and derivatized hyaluronic acid (HA, Fida Advanced Biopolymers, Italy) scaffolds were prepared using solvent casting/particulate leaching and phase inversion/particulate leaching techniques, respectively. A 20% solution of PLLA in methylene chloride and a 10% solution of HA in N-methyl pyrrolidone were each mixed with sodium chloride crystals (106–600 um) at a salt to polymer ratio (w/w) of 15:1. The PLLA mixture was molded, air dried, washed in distilled water, and dried, all for 24 hours. The HA mixture was washed in distilled water and lyophilized, each for 48 hours. Scaffolds were trimmed to a thickness of 1.5 mm and a diameter of 5 mm, and sterilized by steam autoclaving.

2. BMP2/Scaffold Construct Preparation

Recombinant human bone morphogenetic protein-2 (rhBMP2, a gift from Genetics Institute, 4.4 pg) was coated on HA and PLLA scaffolds in 3 ways: (1) BMP precoating and drying (HA P or PLA P), (2) BMP and collagen gelled together in situ (HA SCB or PLA SCB), and (3) BMP precoating followed by the addition of collagen (PC). For all three preparations, scaffolds were prewet in ethanol and rinsed in sterile saline and loaded with 4.4 ug rhBMP2. For collagen containing scaffolds, 25 ul collagen I (Vitrogen, Collagen Corp.) was used. Scaffolds (HA S or PLA S) alone served as a control.

3. BMP Release Bioassay by Alkaline Phosphatase (AP) Induction of Pluripotent Stem Cells In order to assess the amount and bioactivity of rhBMP2 released from scaffolds, an alkaline phosphatase assay was used. C3H10T1/2 murine embryonic fibroblasts (ATCC) were cultured in Basal Eagle media (Sigma) with 10% FBS. Scaffolds were placed on membrane inserts (3.0 um pore size, Fisher) and incubated in 24 well plates containing 12,500 cells/cm$^2$. Scaffolds were incubated with cells for either 24 or 48 hours and transferred to freshly plated cells after each time point for up to 48 days. Cells that had been incubated with scaffolds containing BMP were cultured for a total of 4 days. At each time point, cells were lysed in 0.1% Triton X-100 buffer and assayed for alkaline phosphatase activity using p-nitrophenol phosphate and read spectrophotometrically at 410 nm. Specific activity was normalized by total protein and expressed as ug/hr/mg protein. Scaffold alone (S), cells alone (control), and collagen gel alone (collagen) served as negative controls, while one time dose of soluble 1 ug/ml BMP served as positive control.

Figure 2:
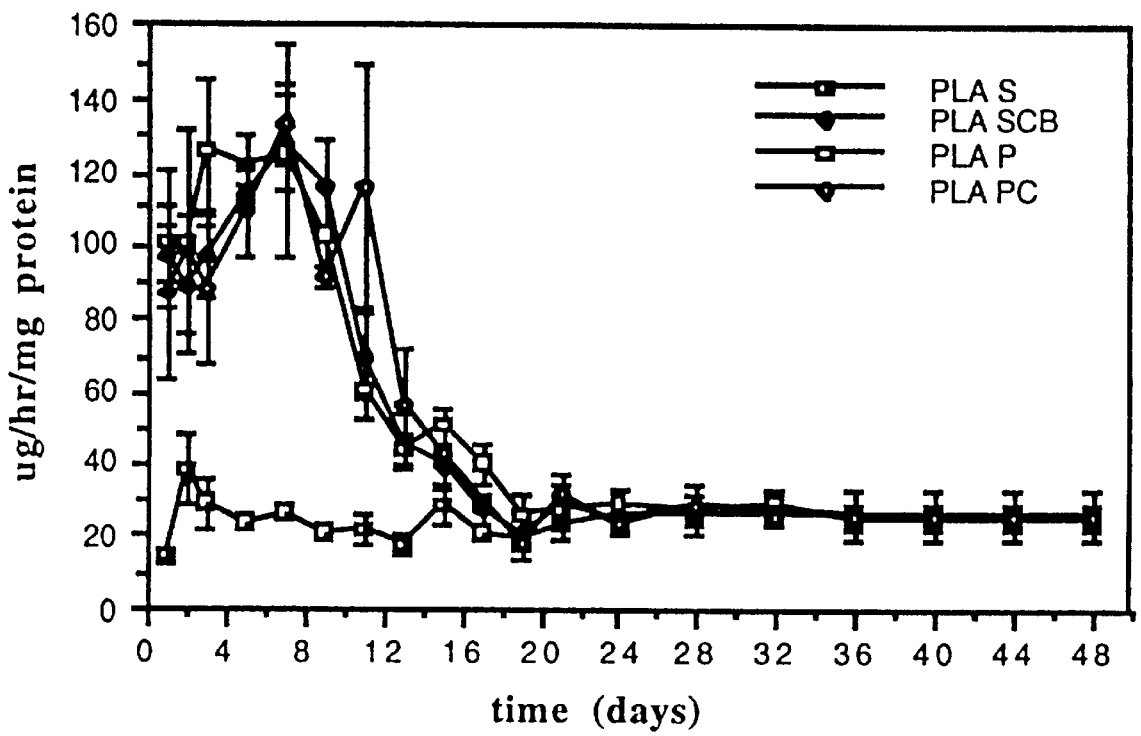
FIG. 2 is a graph depicting the release of BMP from Poly-lactic Acid scaffolds, prepared as a scaffold alone (PLA S), as a scaffold precoated with BMP and dried (PLA P), as a scaffold in which BMP and collagen are gelled together (PLA SCB), and a scaffold in which the scaffold is precoated with BMP and then collagen (PLA PC)

4. Results: The release of rhBMP-2 by the various scaffolds was determined by the ability of the scaffold to stimulate stem cell induction. Hyaluronic acid scaffolds released minimal levels of rhBMP-2 as assessed by their inability to stimulate stem cell induction (FIG. 1). Even after 14 days in vitro, little induction was seen. In contrast, PLLA scaffolds and collagen gels released significant levels of BMP for up to 2 weeks (FIG. 2). This level of induction was comparable to that seen with 1 ug soluble BMP. These results demonstrate that scaffolds can be engineered to locally sequester BMP and suggest that hyaluronic acid scaffolds are superior to poly-L-lactic acid or collagen in their ability to retain BMP.

Scaffolds that sequester BMP at the repair site may show superior bone healing or fusion. Increased BMP concentrations within the scaffold should promote more vigorous cell invasion and bone induction. BMP is available within the scaffold to act locally due to decreased diffusion of BMP out of the scaffold and into the surrounding tissues or bloodstream. Loss of BMP due to diffusion may not only decrease the scaffold's potency, but also lead to potential bone formation at other unwanted sites. Enhanced BMP retention in HA may be attributed in part to ionic interactions where the negatively charged side groups in HA interact with the positively charged N-terminal region of rhBMP2. These results demonstrate that scaffold chemistry is important in sequestering BMP and that hyaluronic acid scaffolds are superior to poly-L-lactic acid or collagen in their ability to retain BMP.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for forming a substrate having interconnected pores for cell growth, comprising:

dissolving a water-insoluble ester derivative of hyaluronic acid in a first solvent, forming a mixture of the first solvent, the water-insoluble ester derivative of hyaluronic acid and a pore forming agent that is insoluble in the first solvent, contacting the mixture with a second solvent, wherein the water-insoluble ester derivative of hyaluronic acid is insoluble in the second solvent but the pore forming agent is soluble in the second solvent, whereby the first solvent and the pore forming agent are extracted from the mixture to form a porous scaffold of the water-insoluble ester derivative of hyaluronic acid, and drying the scaffold under vacuum from a wet state at a temperature between 4° C. and 37° C.

2. The method of claim 1, wherein the pore forming agent is sized so as to leave voids sufficient to permit cell ingrowth into the scaffold when the pore forming agent is extracted from the mixture.

3. The method of claim 2 wherein the scaffold is dried at ambient temperatures.

4. The method of claim 1, wherein the water-insoluble ester derivative of hyaluronic acid is a covalent conjugate of hyaluronic acid esterified with a benzyl moiety.

5. The method of claim 1 further comprising coating the scaffold with a bioerodable polymer.

6. The methods of claim 1 further adding a compound selected from the group consisting of drugs, growth factors, peptides, proteins, cytokines, oligonucleotides, antisense oligonucleotides, DNA and polymers.

7. The method of claim 6, wherein the compound is added by coating the porous scaffold with the compounds.

8. The method of claim 6, wherein the compound is added by covalent attachment to the porous scaffold.

* * * * *